US008575543B2

(12) United States Patent
Kanie

(10) Patent No.: US 8,575,543 B2
(45) Date of Patent: Nov. 5, 2013

(54) METHOD FOR ANALYZING STRUCTURE OF SUBSTANCE

(75) Inventor: Osamu Kanie, Tokyo (JP)

(73) Assignee: Japan Science and Technology Agency, Saitama (JP)

( * ) Notice: Subject to any disclaimer, the term of this patent is extended or adjusted under 35 U.S.C. 154(b) by 0 days.

(21) Appl. No.: 13/818,141

(22) PCT Filed: Sep. 7, 2011

(86) PCT No.: PCT/JP2011/070322
§ 371 (c)(1),
(2), (4) Date: Feb. 21, 2013

(87) PCT Pub. No.: WO2012/033111
PCT Pub. Date: Mar. 15, 2012

(65) Prior Publication Data
US 2013/0153760 A1    Jun. 20, 2013

(30) Foreign Application Priority Data

Sep. 7, 2010   (JP) .................................. 2010-199676

(51) Int. Cl.
*B01D 59/44* (2006.01)
*H01J 49/26* (2006.01)

(52) U.S. Cl.
USPC ......................................... 250/282; 250/290

(58) Field of Classification Search
USPC ................... 250/281, 282, 290, 293
See application file for complete search history.

(56) References Cited

U.S. PATENT DOCUMENTS 7,541,575 B2 *  6/2009  Lock et al. .................... 250/281

FOREIGN PATENT DOCUMENTS

JP    2010-133707         6/2010
JP    2010133707 A  *    6/2010

OTHER PUBLICATIONS

Shiori, et al. "Mechanism of a Gas-Phase Dissociation Reaction of 4-Aminobutyl Glycosides Under CID MS/MS Conditions", Journal of Mass Spectrometry, 2008, 43, 1132-1139.*
Daikoku et al, "Ion-Trap Mass Spectrometry Unveils the Presence of Isomeric Oligosaccharides in an Analyte: Stage-Discriminated Correlation of Energy-Resolved Mass Spectrometry", Carbohydrate Research 344 (2009) 384-394.*
S. Daikoku et al., "J. Am. Soc. Mass Spectrom.", 18, 2007, pp. 1873-1879.
Y. Shioiri et al., "J. Mass Spectrom.", 43, 2008, pp. 1132-1139.
Y. Shioiri et al., "Anal. Chem.", 81, 2009, pp. 139-145.
Y. Takegawa et al., "Anal. Chem.", 76, 2004, pp. 7294-7303.
A. Kameyama et al., "Anal. Chem.", 77, 2005, pp. 4719-4725.

(Continued)

*Primary Examiner* — Robert Kim
*Assistant Examiner* — David E Smith
(74) *Attorney, Agent, or Firm* — Greenblum & Bernstein P.L.C.

(57) ABSTRACT

A method for analyzing a structure of a substance of interest uses triple-quadrupole mass spectrometry (TQ-MS), and allows for acquisition of $MS^n$ information from data resulting from the TQ-MS measurement. The method includes (a) performing a measurement of triple quadrupole mass spectrometry with respect to the substance of interest while varying a value of CID energy; (b) at given values of CID energy, calculating percentages of precursor ion contents to a total ion content, and percentages of product ion contents to the total ion content; (c) extracting values of the percentages of product ion contents to the total ion content, wherein said values are values of the percentages of product ion contents at the respective values of CID energy; and (d) calculating sums of all combinations of the values of the percentages of product ion contents to the total ion content extracted in step (c).

7 Claims, 5 Drawing Sheets

(56) References Cited

OTHER PUBLICATIONS

D. Ashline et al., "Anal. Chem.", 77, 2005, pp. 6250-6262.
A. Kurimoto et al., "Anal. Chem.", 78, 2006, pp. 3461-3466.
S. Daikoku et al., "Carbohydr. Res.", 344, 2009, pp. 384-394.
O. Kanie et al., "Multi-stage mass spectrometric information obtained by deconvolution of energy-resolved spectra acquired by triple-quadrupole mass spectrometry", Rapid Communications in Mass Spectrometry, vol. 25, Issue 11, May 3, 2011, pp. 1617-1624.
G. Siuzdak et al., "Proc. Nat'l Acad. Sci. USA", 91, 1994, pp. 11290-11297.
M.R.J. et al., "Am. Soc. Mass Spectrom", 10, 1999, pp. 175-183.
S.P. Gygi, "R. Chem. Biol.", 4, 2000, pp. 489-494.
S.G. Villas-Boas et al., "J. Mass Spectrom Rev.", 24, 2005, pp. 613-646.
W.A. Korfmacher, "Drug Discovery Today", 10, 2005, pp. 1357-1367.
R.E. March, "Mass Spectrom. Rev.", 28, 2009, pp. 961-989.
K.R. Jonscher 1 et al., "Anal. Biochem.", 244, 1997, pp. 1-15.
R.E. March, "Int. J. Mass Spectrom", 200, 2000, pp. 285-312.
R.E. March, "Rapid Commun. Mass Spectrom.", 12, 1998, pp. 1543-1554.
O. Kanie et al., "Proc. Jpn. Acd. Ser. B", 85, 2009, pp. 204-215.
S. Hase et al., "Biochem. Biophys. Res. Commun.", 85, 1978, pp. 257-263.
International Preliminary Report on Patentability and English language translaton thereof, mail date is Apr. 9, 2013.
Japan Office Action and English language translaton thereof, mail date is Jan. 8, 2013.

* cited by examiner

METHOD FOR ANALYZING STRUCTURE OF SUBSTANCE

TECHNICAL FIELD

The present invention relates to a method for analyzing a structure of a substance of interest, wherein a measurement of triple quadrupole mass spectrometry is performed with respect to the substance of interest, and a predetermined deconvolution process is performed with respect to the resulting data to analyze the structure of the substance of interest.

BACKGROUND ART

Triple-quadrupole mass spectrometry (TQ-MS) has been frequently used in combination with high-performance liquid chromatography (HPLC) interfaced with the electrospray ionization (ESI) method (see Siuzdak, G. Proc. Natl. Acad. Sci. USA 1994, 91, 11290-11297; Yu, X., Cui, D., Davis, M. R. J. Am. Soc. Mass Spectrom. 1999, 10, 175-183; Gygi, S. P., Aebersold, R. Chem. Biol. 2000, 4, 489-494; Villas-Boas, S. G., Mas, S., Akesson, M., Smedsgaard, J., Nielsen, J. Mass Spectrom. Rev. 2005, 24, 613-646; Korfmacher, W. A. Drug Discovery Today 2005, 10, 1357-1367). Such a liquid chromatography-mass spectrometry (LC-MS) system can be used to acquire structural information, as it facilitates the analysis of the fragmentation of an ion under collision-induced dissociation (CID) conditions. Furthermore, from a retention time of a given species in the chromatography column, it is possible to determine affinity of the species for a stationary phase used in the HPLC and to thus acquire information on the structure. However, this technique is disadvantageous that said technique provides only MS/MS information. Additionally, Quadrupole ion trap mass spectrometry (QIT-MS) allows for multistage MS/MS analysis which provides in-depth structural information (see Gygi, S. P., Aebersold, R. Chem. Biol. 2000, 4, 489-494; Villas-Boas, S. G., Mas, S., Akesson, M., Smedsgaard, J., Nielsen, J. Mass Spectrom. Rev. 2005, 24, 613-646; March, R. E. Mass Spectrom. Rev. 2009, 28, 961-989; Jonscher1, K. R., Yates III, J. R. Anal. Biochem. 1997, 244, 1-15; March R. E. Int. J. Mass Spectrom. 2000, 200, 285-312; March R. E. Rapid Commun. Mass Spectrom. 1998, 12, 1543-1554). However, it is practically difficult to perform multistage MS/MS experiments during the period of elution of a compound in the HPLC analysis. Accordingly, in order to gain new insights into structural information within time required for the HPLC analysis, it is important to overcome a disadvantage of TQ-MS, which does not allow for sequential mass spectral analysis ($MS^n$).

In the past, energy-resolved mass spectrometry (ERMS) using QIT-MS has been investigated in order to develop a method elucidating structures of complex glycans and configurations of glycosidic linkages. In most cases, ERMS spectra acquired for sodiated ions of various oligosaccharides are simple, with a series of peaks corresponding to a precursor ion and a plurality of product ions. These peaks are analyzed and approximated by using Boltzmann sigmoidal equations (see Kurimoto, A., Daikoku, S., Mutsuga, S., Kanie, O. Anal. Chem. 2006, 78, 3461-3466; Daikoku, S., Ako, T., Kato, R., Ohtsuka, I., Kanie, O. J. Am. Soc. Mass Spectrom. 2007, 18, 1873-1879; Shioiri, Y., Suzuki, K., Kanie, O. J. Mass Spectrom. 2008, 43, 1132-1139; Shioiri, Y., Kurimoto, A., Ako, T., Daikoku, S., Ohtake, A., Ishida, H., Kiso, M., Suzuki, K., Kanie, O. Adnal. Chem. 2009, 81, 139-145). More complex ERMS spectra may be acquired in rare cases. In the course of elucidating gas-phase reactions of glycans, it has been revealed that a complex spectrum was acquired therein and that the $MS^n$ spectrum contained some information regarding fragmentation reactions of a product ion (information of $MS^{n+1}$) which was not usually acquired in a CID process of QIT-MS. Such information, however, is considered less important for a QIT-MS analysis because a QIT-MS apparatus can be used to perform $MS^n$ experiments. In contrast, the aforementioned $MS^{n+1}$ information will be very important for a TQ-MS analysis, as a TQ-MS apparatus cannot be used for $MS^n$ experiments. Additionally, such $MS^{n+1}$ information would also be useful when the TQ-MS method is used in combination with HPLC for structure elucidation.

SUMMARY OF THE INVENTION

The object of the present invention is to provide a method for analyzing a structure of a substance of interest, using triple-quadrupole mass spectrometry (TQ-MS), the method which allows for acquisition of $MS^n$ information from data resulting from the TQ-MS measurement.

The present inventor had conducted intensive studies to solve the aforementioned problem, and, consequently, discovered that $MS^n$ information can be acquired by way of calculating ratios of product ion contents to the total ion content with respect to an ERMS spectrum acquired in a TQ-MS measurement; and performing a linear regression analysis to sums of any arbitrary combinations of said ratios of product ions, whereby $MS^n$ information can be acquired. The present invention was completed based on this discovery.

More specifically, an aspect of present invention relates to the followings.

[1]. A method for analyzing a structure of a substance of interest, including:

(a) performing a measurement of triple quadrupole mass spectrometry with respect to the substance of interest while varying a value of CID energy;

(b) at given values of CID energy, calculating percentages of precursor ion contents to a total ion content, and percentages of product ion contents, each having specific m/z values, to the total ion content;

(c) extracting values of the percentages of product ion contents, each having specific m/z values, to the total ion content, wherein said values are values of the percentages of product ion contents at the respective values of CID energy which give respective values of the percentages of the precursor ion contents to the total ion content calculated in step (b);

(d) calculating sums of all combinations of the values of the percentages of product ion contents, each having specific m/z values, to the total ion content extracted in step (c); and (e) from functions where the values of percentages of precursor ion contents to the total ion content are assigned as x and where the calculated values of the sums of combinations are assigned as y, selecting those which can be straight-line approximated, and analyzing the structure of the substance of interest, based on m/z values of product ions which each give the selected functions.

[2] The method according to [1], wherein, in step (b), the values of CID energy are assigned to an X axis and any values of percentages are assigned to a Y axis, and the percentages of precursor ion contents to the total ion content, and the percentages of product ion contents, each having specific m/z values, to the total ion content are plotted therein to generate a graph.

[3] The method according to [1] or [2], wherein, in step (c), while the percentages of precursor ion contents to the total ion content are assigned to an X axis, the percentages of product ion contents, each having specific m/z values, to the total ion content are plotted to the Y-axis direction to generate a graph.

[4] The method according to any one of [1] to [3], wherein, in step (d), while the percentages of precursor ion contents to the total ion content are assigned to an X axis, the calculated values of sums of combinations are plotted to the Y-axis direction to generate a graph.

[5] The method according to any one of [1] to [4], wherein the straight-line approximation in step (e) is performed by using formula (4):

$$Syx = \sqrt{\frac{\sum_{j=1}^{n}(x_j - a_j)(y_j - b_j)}{n-2}} \quad (4)$$

wherein Syx represents a residual of a linear regression curve; $x_j$ and $y_j$ represent coordinates of data j; $a_j$ and $b_j$ represent coordinates of the regression curve; and n−2 is a degree of freedom.

[6] The method according to any one of [1] to [5], wherein $MS^n$ information is acquired in step (e).

[7] The method according to any one of [1] to [6], wherein the substance of interest is a sugar chain.

The present invention allows for acquisition of $MS^n$ information, which had been considered impossible in conventional TQ-MS measurements, and thus enables more detailed structural analysis of a substance of interest.

BRIEF DESCRIPTION OF THE DRAWINGS

FIG. 1a shows a CID spectrum showing that a precursor ion X produces fragment ions ($f_1$-$f_4$). FIG. 1b shown an ERMS spectrum observed for dissociation of an ion X in which the data can usually be analyzed by Boltzmann sigmoidal equations. FIG. 1c shows a graph of replot (ratio plot) of the ERMS of FIG. 1b where the precursor ion X is assigned to the x-axis and the individual product ions are assigned to the y-axis.

FIG. 2a shows an ERMS spectrum of a sodiated ion of methyl ester of a ganglioside GD1a (1). FIG. 2b shows a ratio plot of the ERMS of FIG. 1a. FIG. 2c shows fragmentation of the precursor ion (m/z 1916.1). Some dissociations corresponding to ruptures of several glycosidic linkages were observed where the most abundant ion was a y-ion with an N-acetylgalactosaminyl cleavage.

FIG. 3a shows a dissociation scheme. FIG. 3b shows an ERMS spectrum in which some of the curves of the product ions cannot be approximated by Boltzmann sigmoidal equations. FIG. 3c shows a ratio plot of ERMS in which summation of a series of curves results in a linear curve.

FIG. 4a shows an ERMS spectrum. FIG. 4b shows a ratio plot of the ERMS of FIG. 1a. Closed circles show sums of all product ions. Open squares show sums of ions with m/z 466.2 and m/z 628.3. FIG. 4c shows fragmentation of the precursor ion (m/z 646.3). Some dissociations corresponding to the galactosyl cleavage and dehydration proceeded at PA and N-acetyl group were observed.

FIG. 5a shows an ERMS spectrum. FIG. 5b shows a ratio plot of the ERMS of FIG. 5a. FIG. 5c shows arbitrary summation of intensities of the individual product ions in the ratio plot. FIG. 5d shows fragmentation of the precursor ion (m/z 646.3). Some dissociations corresponding to the galactosyl cleavage ($f_2$) and dehydration that proceeded at the PA and N-acetyl groups ($f_1$ and $f_3$) were observed. In addition, other fragments such as $f_4$-$f_6$, which were not observed during QIT-MS, were observed.

EMBODIMENT FOR CARRYING OUT THE INVENTION

Figure 1:
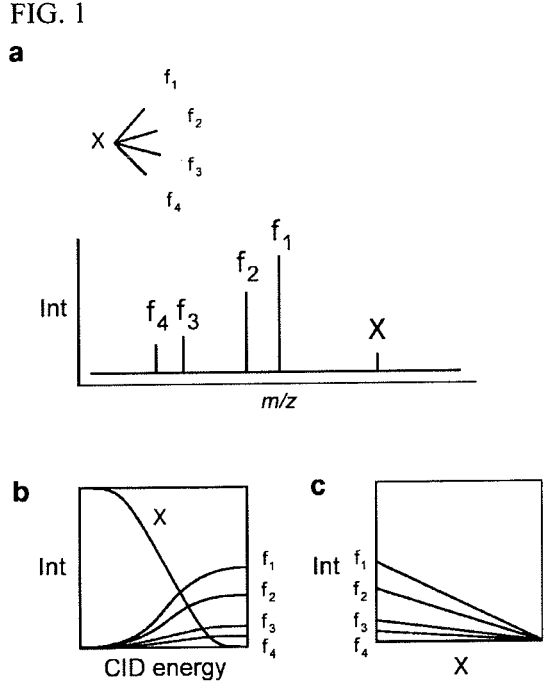
FIG. 1 shows a typical dissociation profile obtained by QIT-MS for an ion X.

The method for analyzing a structure of a substance according to the present invention is characterized in that the method includes: (a) performing a measurement of TQ-MS with respect to the substance of interest while varying a value of CID energy; (b) at given values of CID energy, calculating percentages of precursor ion contents to a total ion content, and percentages of product ion contents, each having specific m/z values, to the total ion content; (c) extracting values of the percentages of product ion contents, each having specific m/z values, to the total ion content, wherein said values are values of the percentages of product ion contents at the respective values of CID energy which give respective values of the percentages of the precursor ion contents to the total ion content calculated in step (b); (d) calculating sums of all combinations of the values of the percentages of product ion contents, each having specific m/z values, to the total ion content extracted in step (c); and (e) from functions where the values of percentages of precursor ion contents to the total ion content are assigned as x and where the calculated values of the sums of combinations are assigned as y, selecting those which can be straight-line approximated, and analyzing the structure of the substance of interest, based on m/z values of product ions which each give the selected functions.

In the present invention, "CID energy (energies)" generally refers to an energy which is applied to cause collision induced dissociation (CID), and specifically refers to a voltage of an alternating electric field of a certain frequency for vibrating ions. "Precursor ion(s)" refer to ion(s) which correspond to a substance of interest as a precursor, and "product ion(s)" refer fragment ion(s), each having m/z value(s), which are obtained by performing a TQ-MS measurement to a precursor ion. Additionally, "m/z" shows a ratio of mass number (m) and charge (z). Additionally, "$MS^n$ information" refers to information on a structure of a precursor ion which is obtained from m/z values, signal intensities, CID energies, etc. of product ions generated by multistage decomposition of the precursor ion.

In the present invention, in step (a), a TQ-MS measurement is performed while varying a value of CID energy, until product ions having specific m/z values, are generated from a precursor ion corresponding to a substance of interest. Preferably, the TQ-MS measurement is performed while varying a value of CID energy until the intensity of the precursor ion becomes about "0" (zero).

The substance of interest, which is a subject for structural analysis according to the present invention, is not particular limited as long as it can be subjected to a TQ-MS measurement. However, it is preferable that the substance of interest be a sugar chain. The sugar chain may be one obtained from biological tissues, cells or the like, or may be one obtained from a sugar chain which binds to a synthesized protein. Furthermore, those obtained by acid hydrolytically or enzymatically degrading these, or those obtained by separating and purifying these by HPLC or the like can also be used. Additionally, chemically synthesized sugar chains can also be used.

Next, in step (b), at given values of the varied CID energy, percentages of precursor ion contents to the total ion content, and percentages of product ion contents of specific m/z values to the total ion content are calculated. Specifically, based on data of the TQ-MS measurement obtained in step (a), percentages of precursor ion intensities to the total ion intensity and percentages of product ion intensities of specific m/z values to the total ion intensity at respective values of CID energy are calculated. That is to say, at a point when initiating the TQ-MS measurement by applying CID energy thereto, the precursor ion content corresponds to the total ion content, and the percentage thereof is 100%.

In step (b), the CID energies may be assigned to an X axis and any percentages may be assigned to a Y axis, and the above obtained percentages of precursor ion contents to the total ion content, and percentages of product ion contents of specific m/z values to the total ion content may be plotted to generate a graph, and an ERMS spectrum relating to a precursor ion and product ions each having m/z values may be acquired. In the present specification, the graph of FIG. 5*a* relating to the examples described below is shown as one example of such an ERMS spectrum. An ERMS spectrum includes a plurality of data points which each have two parameters, CID energies and the above ion contents.

Subsequently, in step (c), values of the percentages of product ion contents, each having specific m/z values, to the total ion content are extracted, wherein said values are values of the percentages of product ion contents at the respective values of CID energy which give the respective values of the percentages of precursor ion contents to the total ion content calculated in step (b).

In step (c), the percentages of precursor ions may be assigned to an X axis, and the percentages of product ions are assigned to a Y axis, and the above extracted values of the percentages of product ion contents, each having specific m/z values, to the total ion content may be plotted thereto to generate a graph. In the present specification, the graph of FIG. 5*b* relating the examples described below is shown as one example of such a graph.

Subsequently, in step (d), sums of all combinations of the values of the percentages of product ion contents, each having specific m/z values, to the total ion content extracted in step (c) are calculated.

In step (d), the percentages of the precursor ion contents to the total ion content may be assigned to an X axis, and the above calculated values of sums of combinations may be plotted to the Y-axis direction to generate a graph. In the present specification, the graph of FIG. 5*c* relating to the examples described below is shown as one example of such a graph. The graph obtained in such a manner includes a plurality of curves which each indicate sums of the percentages directed to the combinations of product ions, each having specific m/z value.

Subsequently, in step (e), from functions where the values of percentages of precursor ion contents to the total ion content are assigned as x and where the values of the sums of combinations calculated in step (d) are assigned as y, those which can be straight-line approximated are selected, and, based on m/z values of product ions which each give the selected functions, the structure of the substance of interest is analyzed.

As described above, when the graph is generated in step (d), among a plurality of functions included in the graph, those which can be straight-line approximated may be selected.

As to techniques for straight-line approximation, various techniques known to those skilled in the art can be used. For example, the straight-line approximation in step (d) can be carried out by using a generally-known least-square technique, namely by using formula (4) or (5).

$$Syx = \sqrt{\frac{\sum_{j=1}^{n}(x_j - a_j)(y_j - b_j)}{n-2}} \quad (4)$$

In Formula (4), Syx represents a residual of a linear regression curve; $x_j$ and $y_j$ represent coordinates of data j, and $a_j$ and $b_j$ represent coordinates of the regression curve. $n-2$ is a degree of freedom. The value for Syx as a threshold can be appropriately determined according to data obtained in the TQ-MS. It is preferable that a value of 2 for Syx be use, and in this case, any curves whose values of Syx are 2 or less will be selected by straight-line approximation.

$$R^2 = \frac{\sum_{j=1}^{n}(x_j - p)(y_j - q)}{\sqrt{\sum_{j=1}^{n}(x_j - p)^2}\sqrt{\sum_{j=1}^{n}(y_j - q)^2}} \quad (5)$$

In Formula (5), $x_j$ and $y_j$ represent coordinates of data j; and p and q represent averages of coordinates of the data, respectively. The value for $R^2$ as a threshold can be appropriately determined according to data obtained in the TQ-MS. It is preferable that a value of 0.90 for $R^2$ be used as a threshold, and, in this case, any curves whose values of $R^2$ are 0.90 or more will be selected by straight-line approximation.

In the present invention, the structure of a substance of interest is analyzed based on m/z values, etc. of product ions which each give functions (curves in a graph) selected by performing straight-line approximation. Specifically, by comparing m/z values, etc. of product ions in combinations giving functions which can be straight-line approximated, which order the product ions had been generated from the precursor ion can be analyzed. For example, assuming that the sample (Galili antigenic trisaccharide) used in the following examples be a compound "X" whose structure has been unknown, according to the present invention, the dissociation pathway and structural information described below can be acquired.

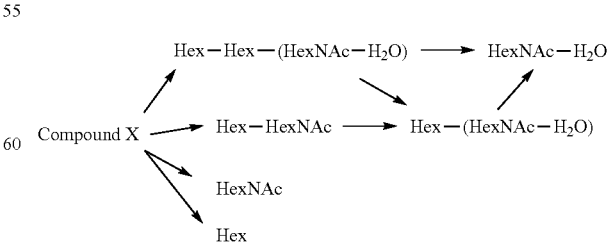

In the above dissociation pathway, "Hex" represents a hexose, and "HexNAc" represents an N-acetyl hexosamine.

Based on the information of the above dissociation pathway, it becomes clear that the structure of compound "X" be Hex-Hex-HexNAc.

Thus, according to analysis of the present invention, $MS^n$ information can be extracted even in a TQ-MS measurement.

The present invention will be described in more detail with reference to the following examples. However, the present invention is not particularly limited to the following examples.

EXAMPLES

<Materials and Methods>
(Materials)

Ganglioside GD1a (1) was purchased from Seikagaku Corp. (Tokyo, Japan), and was esterified. Galili antigenic trisaccharide (2) was purchased from Carbohydrate Synthesis Ltd. (Oxford, UK), and was pyridyl-aminated according to a previously reported procedure (Hase, S., Ikenaka, T., Matsushima, Y, Biochem. Biophys. Res. Commun. 1978, 85, 257-263.).

(Instrumentation (MS) and Data Collection)

Samples were analyzed using quadrupole ion-trap mass spectrometers, Esquire 3000 plus (Bruker Daltonics GmbH, Bremen, Germany) and API Q-Star pulsar i (Applied Biosystems/SCIEX, ON, Canada) equipped with a Pico View ESI (nanospray) source (New Objective, Inc. MA USA) in the positive mode.

The experiments performed using the QSTAR Pulsar i Q-TOF MS apparatus (controlled by Analyst QS) as a TQ-MS measurement were as follows. Data collection was carried out in the positive mode with a full scan between m/z 100 and 2000. Samples (1 pmol/µL) were dissolved in MeOH, and introduced into an ion source with a coated nanospray tip (New Objective, Inc. MA, USA) at a flow rate of 150 nL/min. A typical ion spray voltage for nanospray was 1600 V. Nitrogen gas was used as the curtain gas (15 psi) as well as the collision gas. The collision-induced dissociation (CID) measurements were performed at the instrumental parameter CAD=2, which corresponds to $2.8 \times 10^{-3}$ torr at the collision gas pressure and with collision energies ranging from 23 eV to 69 eV, depending upon the charge state and m/z value of a precursor ion. The first and second declustering potentials, i.e., DP1 and DP2, were 50 V and 15 V, respectively, and the focusing potential was 250 V. MS/MS spectra were acquired using the selection of the precursor ion by the quadrupole in a low-resolution mode (less than unit resolution). Consequently, the entire isotopic cluster of the parent was sent into the collision cell, thereby obtaining the isotopic clusters for all the fragments. All the spectra reported herein were averages of scans for 1.0 min.

Meanwhile, detailed experimental conditions for mass spectrometric analysis using a QIT-MS/MS with quadrupole ion-trap mass spectrometers, Esquire 3000 plus were reported previously (Kanie, O., Kurimoto, A., Kanie, Y., Daikoku, S., Ohtake, A., Suzuki, K., Proc. Jpn. Acd. Ser. B 2009, 85, 204-215).

(General Data Handling)

In order to obtain graphs of the ERMS, equation (1) given below was used. When an ion "$I_P$" produced a series of product ions, $I_1, I_2, I_3, \ldots I_i$, the relative ion currents for individual ions were defined by said equation (1). By using said equation (1), ERMS spectra of the present invention (FIG. 5a) are obtained.

$$^{rel}C = \frac{C_{I_i}}{C_{I_P} + \sum_{i=1}^{n} C_{I_i}} \times 100 \qquad (1)$$

wherein $^{rel}C$ represents an ion current (%) of a particular ion among observed ions, and is expressed as a percentage of the total ion current. $C_{I_i}$ is an ion current observed in a focus, and $C_{I_P}$ represent an ion current of a precursor ion. Calculations were performed using a program that had been developed with Excel (Excel 2000, Microsoft Corp. Washington, USA). Said program was based on the DSUM function, and was programmed to choose a range of isotopes (w) to be taken into consideration (w=2 in the experiments).

Figure 5:
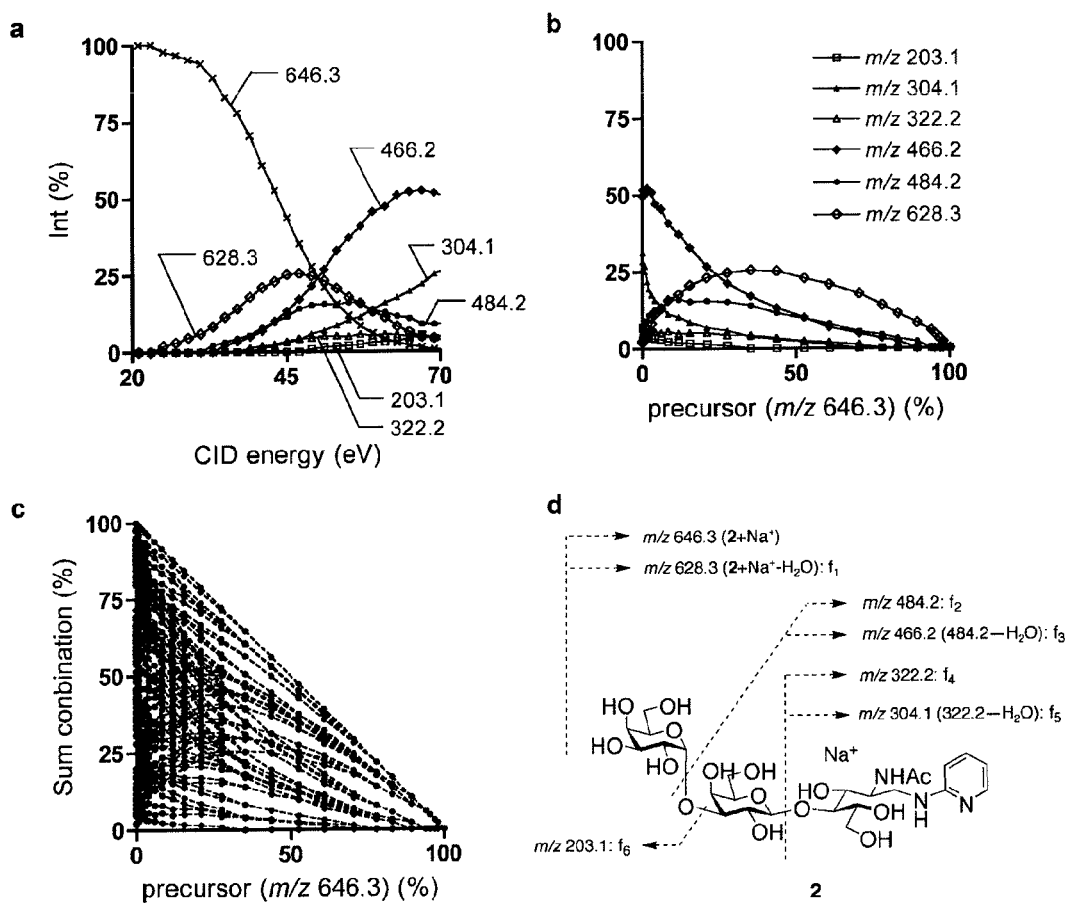
FIG. 5 shows an ERMS spectrum of [2+Na]⁺ obtained on TQ-MS.

$^{rel}C$ was plotted versus $C_{I_P}$ to obtain the graph shown in FIG. 5b. The individual intensities of the peaks of the precursor ion and product ions are normalized in a percentage, and can thus be expressed by Equation (2) below.

$$\sum_{i=1}^{n} {}^{rel}C_{I_i} = 100 - {}^{rel}C_{I_P} \qquad (2)$$

When the fragment ion ($I_i$) is produced independently; in other words, when all the fragment ions are directly produced from a precursor, the intensity of each ion can be described by Equation (3) below:

$$^{rel}C_{I_i} = n(100 - {}^{rel}C_{I_P}) \qquad (3)$$

wherein $0 < n \leq 1$.

When $^{rel}C_{I_i} = 0 (x=0)$ (the precursor ion no longer exists), y-intercept ($^{rel}C_{I_i}$) is the maximum response of $I_i$, or is the "ideal" intensity of $I_i$. Thus, the curves of respective fragments can be fitted with a linear function. This means that the data point collected for the ERMS experiments can be minimized.

When $I_i$ is not independent, the ratio of each product ion to the precursor ($I_p$) over a range of CID energies is not in a linear relationship. In this case, the summation of an arbitrary combination of $I_p$ becomes a linear relationship. Therefore, C(m, 1) of 1 ions of $I_i$ from all the m ions were considered, respective data for such combinations were plotted to generate a graph (FIG. 5c), and standard deviation of the residuals (Syx) of a linear regression curve was examined. The residuals (Syx) of the linear regression curve are expressed by Equation (4) below.

$$Syx = \sqrt{\frac{\sum_{j=1}^{n}(x_j - a_j)(y_j - b_j)}{n - 2}} \qquad (4)$$

$x_j$ and $y_j$ represent coordinates of data j. $a_j$ and $b_j$ represent coordinates of a regression curve. n−2 is a degree of freedom. Furthermore, when the intensity of a precursor ion is 100%, the intensities of any product ions will be 0%. Thus, a regression curve that passes through the coordinates (x, y)=(100, 0) was considered. When Syx≈0, there exists a strong relationship between the ions. In addition, Syx=2 was used as a threshold in the present experiment.

<Results>
Linear Relationship Between Fragment-ion-to-precursor Ratios Obtained for a Wide Range of CID Energies.

At first, the MS/MS analysis of a precursor ion X under CID conditions is considered (FIG. 1a). The obtained spectrum (FIG. 1a) provides the intensities of the individual signals of ions. One might obtain the ratios of such signals for comparison, in order to determine the structure of an unidentified compound. On the other hand, the ERMS analysis of ion X under CID conditions (FIG. 1b) provides information related to the activation energy required for the rupture of the precursor ion, in addition to the information that can be obtained by ordinary MS/MS analysis. In view of this fact, it might be possible to extract information related to the chemical reactions occurring in a collision cell. A series of curves with a linear relationship can be seen in the second plot, which shows percentages of individual ions to percentages of the precursor ion (FIG. 1c). In such a case, important information that the ratio of the intensities of fragment ions to the precursor is constant, regardless of the applied CID energies, can be obtained. This result suggests that it is possible to compare MS/MS spectra, obtained at different CID energies, with each other, and a very important basis for comparisons of the ratios of fragment peaks in structural determination of a complex glycan is obtained (Takegawa, Y., Deguchi, K., Ito, S., Yoshioka, S., Sano, A., Yoshinari, K., Kobayashi, K., Nakagawa, H., Monde, K., Nishimura, S.-I. Anal. Chem. 2004, 76, 7294-7303; Kameyama, A., Kikuchi, N., Nakaya, S., Ito, H., Sato, T., Shikanai, T., Takahashi, Y., Takahashi, K., Narimatsu, H. Anal. Chem. 2005, 77, 4719-4725; Ashline, D., Singh, S., Hanneman, A., Reinhold, V. Anal. Chem. 2005, 77, 6250-6262). It should be noted that such linearities for different CID energies was generally found in this type of ERMS spectra (FIG. 1b), as was observed for most of the analytes in previous experiments (Kurimoto, A., Daikoku, S., Mutsuga, S., Kanie, O. Anal. Chem. 2006, 78, 3461-3466; Daikoku, S., Ako, T., Kato, R., Ohtsuka, I., Kanie, O. J. Am. Soc. Mass Spectrom. 2007, 18, 1873-1879; Shioiri, Y., Suzuki, K., Kanie, O. J. Mass Spectrom. 2008, 43, 1132-1139; Shioiri, Y., Kurimoto, A., Ako, T., Daikoku, S., Ohtake, A., Ishida, H., Kiso, M., Suzuki, K., Kanie, O. Anal. Chem. 2009, 81, 139-145).

Figure 2:
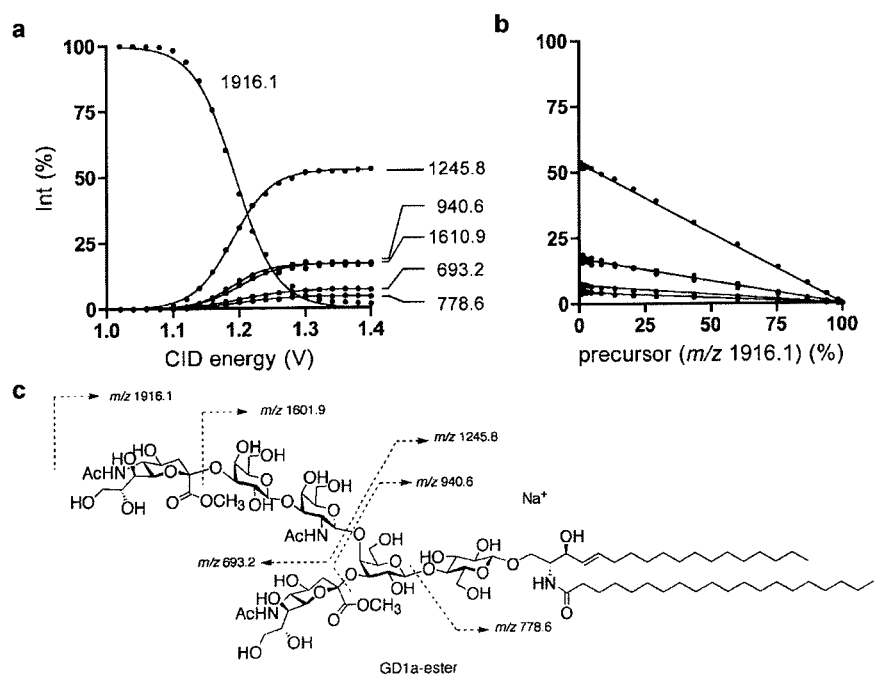

Hereinafter, an analysis of ERMS obtained using a QIT-MS apparatus will be described. The dissociation reaction of methyl ester of a ganglioside GD1a (compound 1) can be considered as a typical example of those which follows a "simple" fragmentation process (FIG. 2). It was observed that a number of fragment ions (m/z 1610.9, 1245.8, 940.6, 778.6, and 693.2) were formed from sodiated 1 (m/z 1916.1: [M+Na]$^+$) under CID conditions. The individual series of data points were well fitted using Boltzmann sigmoidal equations. The precursor-product relationship (ratio plot) is shown in FIG. 2b, indicating that the fragment-ion-to-precursor ratios are constant over a wide range of CID energies.

The Non-linear Relationship Between the Fragment-ion-to-precursor Ratios in ERMS is Attributed to the Fragmentation of the Fragments.

Figure 3:
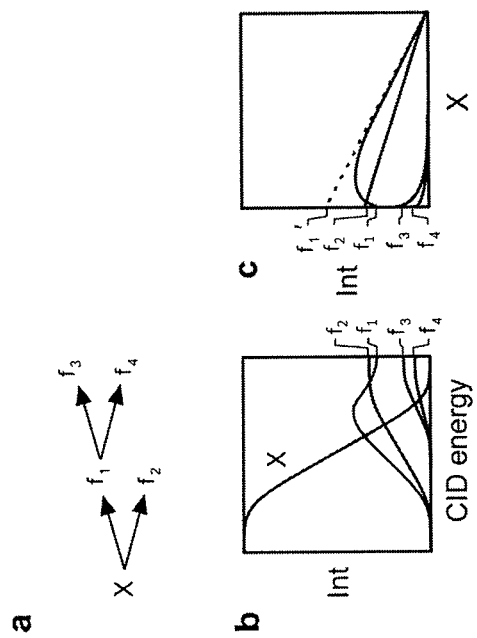
FIG. 3 shows an ERMS of dissociation of an ion X where one of the product ions ($f_1$) further dissociates into $f_3$ and $f_4$.

In some rare cases, complex ERMS spectra as shown in FIG. 3 are obtained. The use of such data has been problematic in a quantitative analysis of ERMS because of the difficulty of approximation, and they have not been used for such an analysis even though these spectra themselves can be considered "structural fingerprints" (Daikoku, S., Kurimoto, A., Mutsuga, S., Ako, T., Kanemitsu, T., Shioiri, Y., Ohtake, A., Kato, R., Saotome, C., Ohtsuka, I., Koroghi, S., Sarkar, S. K., Tobe, A., Adachi, S., Suzuki, K., Kanie, O. Carbohydr. Res. 2009, 344, 384-394). In such a case, some of the fragment-ion-to-precursor ratios show linearity, and others do not, and the sum ($f_1'$) of some of the signal intensities ($f_1$, $f_3$, and $f_4$) becomes linear (FIG. 3c). It was considered that fragment ions $f_3$ and $f_4$ were produced from $f_1$ at a point at which the curve of $f_1$ departs from the dotted line ($f_1'$). This result suggests that the fragmentation reactions of a fragment ion begin to occur at the CID energy corresponding to the point of departure from the line.

Figure 4:
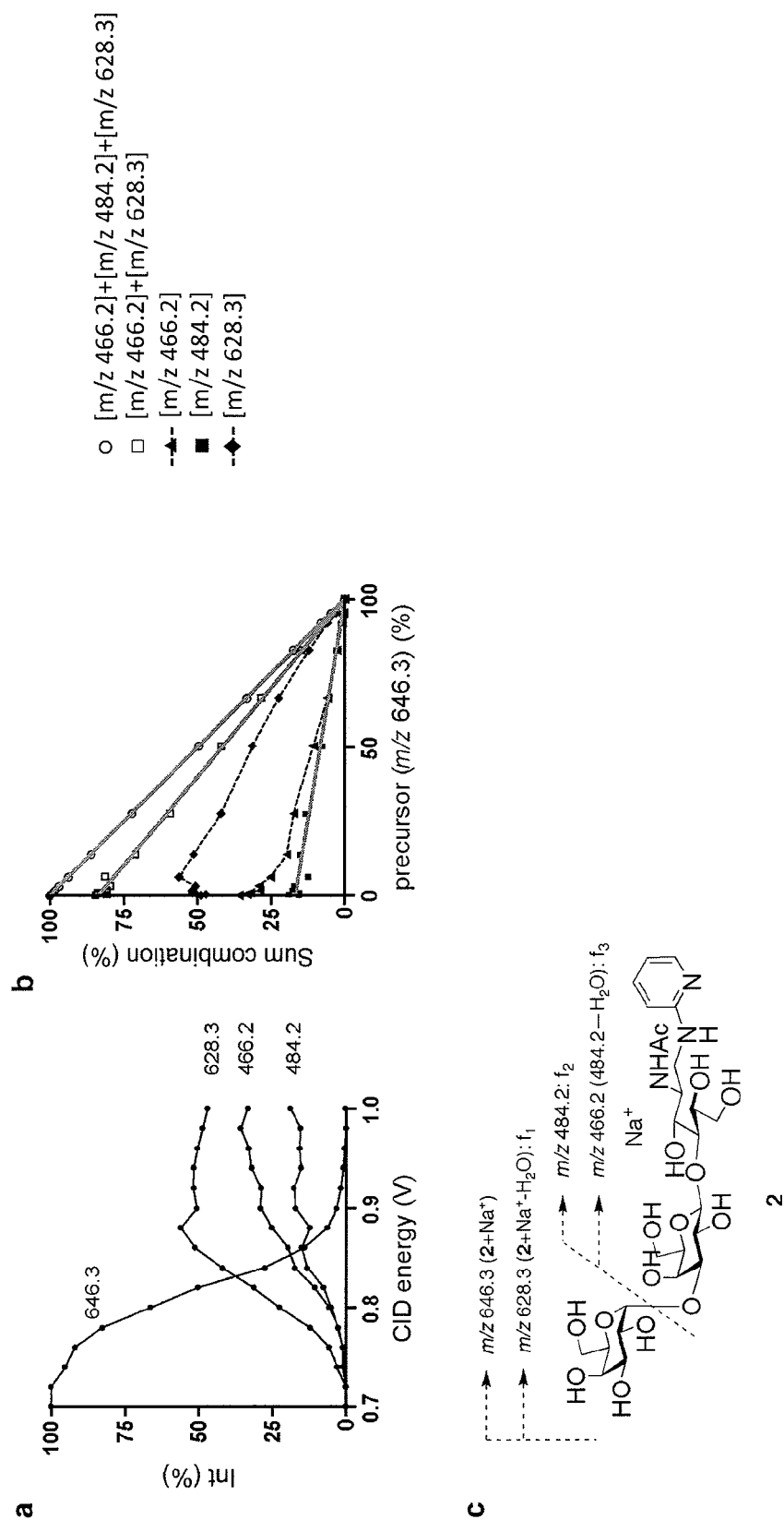
FIG. 4 shows an ERMS spectrum of [2+Na]⁺ obtained on QIT-MS.

A pyridyl-aminated trisaccharide derivative (Galili antigen; 2) was observed as a sodium-adducted species (m/z 646.3), and was then subjected to the ERMS experiment using QIT-MS (FIG. 4a). At first glance, it seemed that there might be some correlation between the generation of fragment ions with m/z 628.3 ($f_1$) and 466.2 ($f_3$). To confirm this, summations of the peak intensities of these fragment ions were obtained (FIG. 4b; the open square symbols represent the sum of these two ions, and closed circles are the sum of all fragments.). The fact that the sum of the intensities of $f_1$ and $f_3$ can be fitted with a linear function indicates that these ions have a close relationship with each other. Furthermore, from the ERMS profile of these ions, it is obvious that the fragment ion with m/z 466.2 was produced from an ion with m/z 628.3 as well as from an ion with m/z 646.3 (original precursor).

MS$^n$ Information Which is Contained in MS/MS Spectrum Obtained by Triple Quadrupole MS.

Since potential utility of the analytical method of obtaining a fragmentation pathway by examining summation of the intensities of selected fragment ions was proved as described above, subsequently, the ERMS spectrum of the ion [2+Na]$^+$ was investigated using TQ-MS. The profile of the ERMS spectrum thus obtained by using TQ-MS was quite different from that obtained by QIT-MS, and was also more complex (FIG. 5a). In addition to the obvious difference between the "generation curves" of the individual fragment ions, ions with m/z 304.1 and 322.2, which were not observed in the QIT-MS experiments, were observed in the present case. Moreover, it was considered that ions with m/z 628.3 ($f_1$) and 466.2 ($f_3$) might have a strong relationship with each other, as observed in the experiment on the QIT-MS. The ratio plot also showed that most of the fragment ions have a non-linear relationship with their precursor (FIG. 5b). Since it was considered that more than one pair of fragment ions were related to one another, combinatorial summations of individual fragment ions were investigated. An arbitrary combination, namely C(m, 1) of ions (1) from entire ions (m), was considered therein, and the standard deviation of the residuals (Syx) of a linear regression curve was investigated in the ratio plot (FIG. 5c). It was considered that the smaller the Syx value, the stronger was the relationship between the selected pair(s) of ions. Combinations of product ions (fragment ions) which constitute curves selected by straight-line approximation, among the curves shown in FIG. 5c, are shown in Table 1. In Table 1, product ions shown by circles are components which constitute respective curves, and Syx values for the respective curves are shown. For example, the series of fragment ions $f_1$-$f_3$ and $f_5$ [m/z 304 ($f_5$), 466 ($f_3$), 484 ($f_2$), and 628 ($f_1$)] showed a certain relationship.

TABLE 1

| Syx value | Fragment ion (m/z) | | | | | |
|---|---|---|---|---|---|---|
| | $f_6$ (203.1) | $f_5$ (304.1) | $f_4$ (322.2) | $f_3$ (466.2) | $f_2$ (484.2) | $f_1$ (628.3) |
| 0.00 | ○ | ○ | ○ | ○ | ○ | ○ |
| 0.49 | ○ | ○ | — | ○ | ○ | ○ |
| 0.49 | — | — | ○ | — | — | — |
| 1.19 | — | ○ | — | ○ | ○ | ○ |
| 1.19 | ○ | — | ○ | — | — | — |
| 1.35 | — | ○ | ○ | ○ | ○ | ○ |
| 1.35 | ○ | — | — | — | — | — |

When taking the ERMS profile as a whole, it was revealed that an ion $f_3$ was produced from $f_2$, which was a product of the precursor $(2+Na^+)$, and that $f_3$ produced $f_5$. This result indicates that the analysis of ERMS data obtained on TQ-MS using the method according to the present invention afforded $MS^3$—and/or $MS^4$—equivalent information. That is to say, while conventional arts had required multiple courses of MS/MS experiments in order to acquire $MS^n$ information, according to the present invention, one course of energy-resolved mass spectrometry (ERMS) using TQ-MS allows for acquisition of $MS^n$ information.

Structural Details.

Form the results in Table 1, the following information can be specifically obtained.

Figure 6:
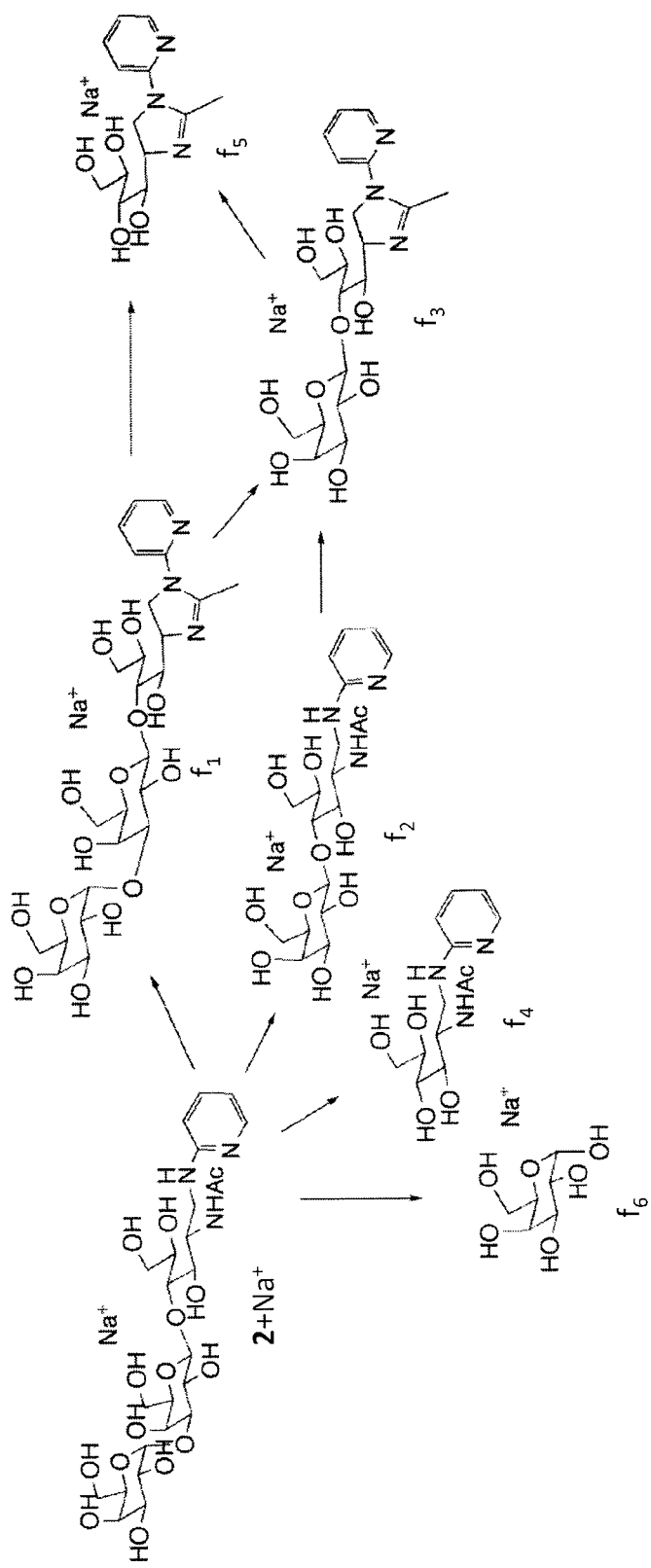
FIG. 6 shows a dissociation pathway of sodiated compound 2 obtained on TQ-MS.

$f_1 = [2+Na^+]$ (precursor: 646)–$H_2O$(18)
$f_2 = [2+Na^+]$–Hex(162) $f_3 = f_1$–Hex, and $f_3 = f_2 - H_2O$
$f_5 = f_1 - 2$Hex, and $f_5 = f_3$–Hex Additionally, "Hex" represents a hexose, and the values in the parentheses represent m/z values or molecular weights. From the above information, information on a dissociation pathway of $[2+Na]^+$ (precursor ion; sample Galili antigenic trisaccharide) could be obtained as shown in FIG. 6.

With regard to the structure of product ions, ions $f_2$ and $f_6$ were compounds with PA residues, and $f_1$, $f_3$, and $f_4$ were dehydrated ions between the PA residues and N-acetyl groups. A hexose-oriented C-ion species ($f_5$) was also observed as a minor signal. The formation of an imidazoline structure under CID conditions was reported previously (Kurimoto, A., Kanie, O. Rapid Commun. Mass Spectrom. 2007, 21, 2770-2778). Although all the fragment ions were consistent with the structure of compound 2, limited information was available from these m/z values alone. The information obtained from the above analysis provided further details, as follows. That is to say, as shown in FIG. 6, the precursor ion $(2+Na^+)$ fragmented into product ions $f_1$, $f_2$, $f_5$, and $f_6$ through the rupture of two glycosidic linkages and dehydration at the reducing terminus. Fragment $f_2$ further yielded $f_3$ and $f_4$ through dehydration and glycosyl rupture. The ion $f_1$ was transformed into $f_4$ by two glycosyl cleavages.

The invention claimed is:

1. A method for analyzing a structure of a substance of interest, comprising:
    (a) performing a measurement of triple quadrupole mass spectrometry with respect to the substance of interest while varying a value of CID energy;
    (b) at given values of CID energy, calculating percentages of precursor ion contents to a total ion content, and percentages of product ion contents, each having specific m/z values, to the total ion content;
    (c) extracting values of the percentages of product ion contents, each having specific m/z values, to the total ion content, wherein said values are values of the percentages of product ion contents at the respective values of CID energy which give respective values of the percentages of the precursor ion contents to the total ion content calculated in step (b);
    (d) calculating sums of all combinations of the values of the percentages of product ion contents, each having specific m/z values, to the total ion content extracted in step (c); and
    (e) from functions where the values of percentages of precursor ion contents to the total ion content are assigned as x and where the calculated values of the sums of combinations are assigned as y, selecting those which can be straight-line approximated, and analyzing the structure of the substance of interest, based on m/z values of product ions which each give the selected functions.

2. The method according to claim 1, wherein, in step (b), the values of CID energy are assigned to an X axis and any values of percentages are assigned to a Y axis, and the percentages of precursor ion contents to the total ion content, and the percentages of product ion contents, each having specific m/z values, to the total ion content are plotted therein to generate a graph.

3. The method according to claim 1, wherein, in step (c), while the percentages of precursor ion contents to the total ion content are assigned to an X axis, the percentages of product ion contents, each having specific m/z values, to the total ion content are plotted to the Y-axis direction to generate a graph.

4. The method according to claim 1, wherein, in step (d), while the percentages of precursor ion contents to the total ion content are assigned to an X axis, the calculated values of sums of combinations are plotted to the Y-axis direction to generate a graph.

5. The method according to claim 1, wherein the straight-line approximation in step (e) is performed by using formula (4):

$$Syx = \sqrt{\frac{\sum_{j=1}^{n}(x_j - a_j)(y_j - b_j)}{n-2}} \qquad (4)$$

wherein Syx represents a residual of a linear regression curve; $x_j$ and $y_j$ represent coordinates of data j; $a_j$ and $b_j$ represent coordinates of the regression curve; and n–2 is a degree of freedom.

6. The method according to claim 1, wherein $MS^n$ information is acquired in step (e).

7. The method according to claim 1, wherein the substance of interest is a sugar chain.

* * * * *